(12) United States Patent
Hinkel et al.

(10) Patent No.: US 9,829,423 B2
(45) Date of Patent: Nov. 28, 2017

(54) CHARACTERIZATION METHODS

(71) Applicant: SCHLUMBERGER TECHNOLOGY CORPORATION, Sugar Land, TX (US)

(72) Inventors: Jerald J. Hinkel, Houston, TX (US); Dean M. Willberg, Salt Lake City, UT (US); Matthew J. Miller, Katy, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 561 days.

(21) Appl. No.: 14/201,461

(22) Filed: Mar. 7, 2014

(65) Prior Publication Data
US 2015/0253234 A1  Sep. 10, 2015

(51) Int. Cl.
*G01N 15/08* (2006.01)

(52) U.S. Cl.
CPC ....... *G01N 15/088* (2013.01); *G01N 15/0893* (2013.01)

(58) Field of Classification Search
CPC .... G01N 15/088; G01N 15/0826; G01N 3/12; E21B 49/00; E21B 47/00; G01V 11/00
USPC ................ 73/38, 37, 152.05, 152, 2, 152.01
See application file for complete search history.

(56) References Cited

U.S. PATENT DOCUMENTS 8,226,747 B2 * 7/2012 Hanamoto ............. B01D 53/02
  502/400
2007/0148044 A1 * 6/2007 Murata ............ G01N 33/54346
  422/82.01
2012/0081838 A1 * 4/2012 Costantino ............... H01B 1/04
  361/502

OTHER PUBLICATIONS

Clarkson, C.R., Jensen, J.L. and Blasingame, T.A. 2011. "Reservoir Engineering for Unconventional Resservoirs: What Do We Have to Consider?" SPE 145080. The Woodlands, TX: SPE. (45 pages).
Clarkson, C.R., Wood, J.M., Burgis, S.W., Aquino, S.D., Freeman, M. and Birss, V. 2012. "Nanopore Structure Analysis and Permeability Predictions for a Tight Gas/Shale Reservoir Using Low-Presssure Adsorption and Mercury Intrustion Techniques." SPE 155537. Pittsburgh, PA: SPE. (18 pages).
Comisky, J.T., Newsham, K.E., Rushing, J.A. and Blasingame, T.A. 2007. "A Comparative Study of Capillary-Pressure-Based Empirical Models for Estimating Absolute Permeability in Tight Gas Sands." SPE 110050. Anaheim, CA: SPE. (18 pages).
Comisky, J.T., Santiago, M., McCollom, B., Buddhala, A. and Newsham, K.E. 2011. "Sample Size Effects on the Application of Mercury Intrusion Capillary Pressure for Determining the Storage Capacity of Tight Gas and Shales." CSUG/SPE 149432. Calgary, Alberta, Canada. (23 pages).

(Continued)

*Primary Examiner* — Lisa Caputo
*Assistant Examiner* — Nigel Plumb
(74) *Attorney, Agent, or Firm* — Andrea E. Tran

(57) ABSTRACT

A method for determining characteristics of a mesoporous material using a desiccation or hydration test is disclosed. The test may involve using a test fluid and exposing sample of a core to a controlled environment, then weighing the samples. The samples may be core samples, comminuted samples, or cuttings. Utilizing the determined characteristics, properties of the mesoporous material, such as porosities, absolute permeabilities and relative permeabilities may be determined.

18 Claims, 3 Drawing Sheets

(56) References Cited

OTHER PUBLICATIONS

Didar, B.R and Akkutlu, I.Y. 2013. "Pore-Size Dependence of Fluid Phase Behavior and Properties in Organic-Rich Shale Reservoirs." SPE 164099. The Woodlands, Texas: SPE. (19 pages).

Elgmati, M., Zheng, H., Flori, R. and Qu, Q. 2011. "Submicron Pore Characterization of Shale Gas Plays." SPE 144050. The Woodlands, TX: SPE. (19 pages).

Greenspan, L. 1976. "Humidity Fixed Points of Binary Saturated Aqueous Solutions." Journal of Research of the National Bureau of Standards, pp. 89-96.

Kuila, U. and Prasad, M. 2011. "Surface Area and Pore Size Distribution in Clays and Shales." SPE 146869. Denver, CO. (13 pages).

Pagels, M., Hinkel, J., and Willberg, D. 2012 "Moving Beyond the Capillary Suction Time Test, SPE 151832." Lafayette, LA, LA: SPE International Forum and Exposition on Formation Damage Control. (13 pages).

\* cited by examiner

CHARACTERIZATION METHODS

BACKGROUND

For modeling gas production from reservoirs, laboratory tests may be performed on samples from the reservoir. Such tests may include determining porosities and absolute permeabilities. Determining porosity may allow for a prediction of an amount of hydrocarbons that may be stored in the porous material. Determining permeability may allow for a prediction of the rate at which a fluid will flow at a given pressure.

In modeling, failure to account for the impact of non-inertial, non-Darcy phenomena, also known as microflows, may lead to errors when attempts are made to model gas production from ultra-low permeability reservoirs such as some shale reservoirs or to interpret results from laboratory tests where a gas is flowed through a sample of material, such as mesoporous material, from these types of reservoirs. Knowledge of the absolute permeability and porosity alone of a porous material may be insufficient to accurately and effectively model flow through a reservoir, particularly when the permeability of the reservoir is ultra-low. Indeed, in some shale specimens, non-inertial, non-Darcy flows may cause the effective permeability of gases to be greater than the absolute permeability. This may cause inaccurate modeling of gas flow through such specimens.

Pore size distribution within porous media may be determined to aid in properly characterizing porous media whose absolute permeabilities are small, such as below one microdarcy. Such porous media are referred to herein as ultra-low permeability media.

In the past, some attempts have been made to measure the pore structure on whole cores with methods involving nitrogen adsorption coupled with mercury intrusion with typically mercury injection capillary pressure (MICP) measurements. These methods were destructive to the cores and thus costly, and they were typically also time consuming.

Another method to determine pore size distribution included nitrogen adsorption. Such a method required the sample be cooled to a very low temperature of 77 K.

SUMMARY

This summary is provided to introduce a selection of concepts that are further described below in the detailed description. This summary is not intended to identify key or essential features or the claimed subject matter, nor is it intended to be used as an aid in limiting the scope of the claimed subject matter.

The statements made merely provide information relating to the present disclosure, and may describe some embodiments illustrating the subject matter of this application.

In aspects, a method is disclosed. The method may be used for determining properties of mesoporous material. The method may include performing, with a test fluid, a desiccation or hydration test on at least a sample of the mesoporous material, and analyzing characteristics of the sample of the mesoporous material.

In further aspects, a method is disclosed. The method may include determining a pore size distribution of a mesoporous material. The method may include performing, with a test fluid, a hydration test on at least a sample of the mesoporous material, and analyzing characteristics of the sample of the mesoporous material to thereby estimate the pore size distribution.

In yet further aspects, a method is disclosed. The method may include performing, with water as a test fluid, a hydration test on at least a sample of the mesoporous material, and analyzing characteristics of the sample of the mesoporous material to thereby estimate the pore size distribution. The performing the hydration test may further include splitting the sample of the mesoporous material and exposing the sample to an environment where a relative humidity of a test fluid is controlled by mixing the water with a salt to form a saturated mixture and controlling a temperature of the saturated mixture.

DETAILED DESCRIPTION OF EMBODIMENTS

Figure 1:
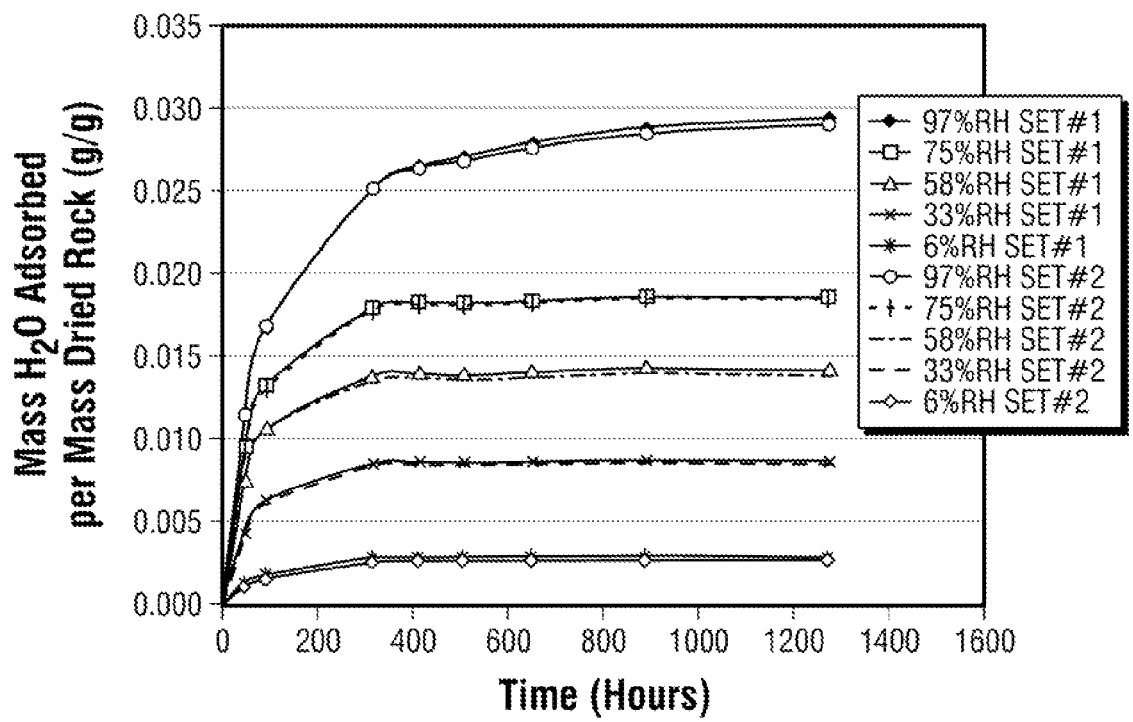
FIG. 1 shows a graphical representation of a hydration test according to one or more embodiments.

In the following description, numerous details are set forth to provide an understanding of the present disclosure. However, it may be understood by those skilled in the art that the methods of the present disclosure may be practiced without these details and that numerous variations or modifications from the described embodiments may be possible.

At the outset, it should be noted that in the development of any such actual embodiment, numerous implementation-specific decisions may be made to achieve the developer's specific goals, such as compliance with system related and business related constraints, which will vary from one implementation to another. Moreover, it will be appreciated that such a development effort might be complex and time consuming but would nevertheless be a routine undertaking for those of ordinary skill in the art having the benefit of this disclosure. In addition, the composition used/disclosed herein can also comprise some components other than those cited. In the summary and this detailed description, each numerical value should be read once as modified by the term "about" (unless already expressly so modified), and then read again as not so modified unless otherwise indicated in context. Also, in the summary and this detailed description, it should be understood that a range listed or described, as being useful, suitable, or the like, is intended to include support for any conceivable sub-range within the range at least because every point within the range, including the end points, is to be considered as having been stated. For example, "a range of from 1 to 10" is to be read as indicating each possible number along the continuum between about 1 and about 10. Furthermore, one or more of the data points in the present examples may be combined together, or may be combined with one of the data points in the specification to create a range, and thus include each possible value or number within this range. Thus, (1) even if numerous specific data points within the range are explicitly identified, (2) even if reference is made to a few specific data points within the range, or (3) even when no data points within the range are explicitly identified, it is to be understood (i) that the inventors appreciate and understand that any conceivable data point within the range is to be considered to have been specified, and (ii) that the inventors possessed knowledge of the entire range, each conceivable sub-range within the range, and each conceivable point within the range. Furthermore, the subject matter of this application illustratively disclosed herein suitably may be practiced in the absence of any element(s) that are not specifically disclosed herein.

The following definitions are provided in order to aid those skilled in the art in understanding the detailed description.

The term "pore size" as used herein refers to a diameter of a pore in a material. The term "pore size distribution" is a measure of the range of pore sizes in a material. The term "porosity" as used herein refers to a ratio of void space to bulk volume.

The term "mesoporous" as used herein is (according to the IUPAC definition) a material having a plurality of pores with pore sizes ranging from 2 to 50 nanometers.

The term "permeability" as used herein refers to a measure of the resistance to the flow of a fluid through a material. A material with ultra-low permeability, as used herein, refers to materials having a measured permeability of 1 microdarcy or less.

The term "comminuted core" refers to a core that has been crushed or ground into smaller fragments. The term "cuttings" refers to small pieces of solid material, for example within a reservoir, removed during drilling.

In embodiments, properties of a material, such as pore site distribution, porosity, and relative and absolute permeability, may be determined by analyzing characteristics of the material. Such characteristics may include, for example, the material's ability to retain or lose fluid that can be determined using laboratory tests.

In embodiments, to determine a pore size distribution of a material, such as a mesoporous material, which can, for instance, be a shale material, certain laboratory tests may be performed. These tests may involve performing desiccation or hydration of one or more samples of the mesoporous material. The mesoporous material may be any mesoporous material, including shale. A sample of the mesoporous material to be tested may be of any shape and any size.

In some embodiments, the laboratory test to be performed on the mesoporous material is a hydration test. Though the following description relates more generally to a hydration test where hydration of a previously dried sample is performed, it will be understood that a desiccation test, where desiccation of a previously saturated sample is performed, can similarly be used to determine the same or similar characteristics.

The sample to be tested can be a full core sample, as comminuted care sample, or a sample of cuttings from a reservoir. The sample to be tested may be obtained, for example, from drill cutting, side-wall cores, or larger cores. In embodiments where a comminuted core sample is used, the amount of time required to perform the test may be reduced. Further, using a comminuted core sample may allow for reduced time to perform the test while still preserving the pore size distributions of the sample as compared to the original core.

In embodiments where a comminuted core sample is used, the sample may be several grams or more. The amount of comminuted core sample to be used may retain properties representative of the formation being evaluated. Further, the particle site of the comminuted core sample may be less than the distance between fissures generally found in shale samples, which may allow for just the shale matrix being involved in the hydration of the sample.

One or more samples from the reservoir may be dried until a constant weight is achieved. For example, drying may continue until three consecutive mass readings for a particular sample agree within the accuracy of the balance used, in some embodiments, the sample may be a sample from a shale reservoir, and the drying is conducted at a temperature near, but generally not exceeding, the temperature of the reservoir from which the sample is taken. It will be within the knowledge of the person skilled in the an to adapt potential surrounding parameters such as salt concentration or pressure.

Hydration of the dried sample may then be performed. The hydration may be performed by exposing the dried sample to an environment where relative humidity and/or vapor pressure of a test fluid is carefully controlled. The sample is exposed to the test fluid, which may be a fluid such as water, methanol, hexane, or any fluid that has an ability to be absorbed by the sample. Other liquids may be used if the test conditions are such that condensation of the vapor may occur. The relative humidity or vapor pressure of an aqueous test fluid can be conveniently controlled by various methods, including saturating the test fluid with various salts, such as those provided by "*Humidity Fixed Points of Binary Saturated Aqueous Solutions," Journal of Research of the National Bureau of Standards,* 1976 at 89-96, to Greenspan et al, incorporated herein by reference, and/or controlling a temperature of the environment. In some embodiments, once the test fluid is saturated with a salt, thereby forming a saturated mixture, the saturated mixture can then be held at a constant temperature and stirred to prevent stratification. Such a process may also involve the saturated mixture remaining saturated by using an excess amount of salt. The excess amount may be selected taking into consideration such factors as the particular salt and the temperature. In some embodiments, the saturation may minimize drift of relative humidity. The relative humidity of the test fluid may be controlled so that the relative humidity over the test period is about 1 to about 98%, or 6 to 97%. The vapor pressure may vary, for example, by using salts and/or controlling temperature.

In some embodiments, the sample is split prior to hydration and each of the split samples are exposed to the environment Where the test fluid has a controlled relative humidity and/or vapor pressure.

The test times for the hydration test may vary based upon the size of the smallest intact portion of the sample. For example, the test time may vary based upon whether the sample is left whole or has been disaggregated. However, the tests may be run on samples of any size or shape, including fragments of sample, as the test times can be adjusted to ensure that the system reaches an equilibrium saturation.

After the initial hydration of the sample, the sample may be weighed at time intervals, such as daily or semi-daily intervals. The frequency of weighing the sample may change (e.g., decrease) over time based upon the amount of weight change shown in previous measurements. The weighing may continue, for example, until no further mass increase is observed. The results may be reported as grams of fluid uptake per gram of sample.

Similarly, though the above example refers to a hydration of a sample, results may be acquired using a desiccation test. Desiccation may occur by initially saturating a sample, and then allowing the sample to dry for a time period. The sample may be weighed at time intervals of such as daily or semi-daily intervals. The frequency of weighing the sample may change (e.g., decrease) over time based upon the amount of weight change shown in previous measurements. The weighting may continue, for example, until no further mass decrease is observed. The results may be reported as grams of fluid loss per gram of sample.

Figure 3:
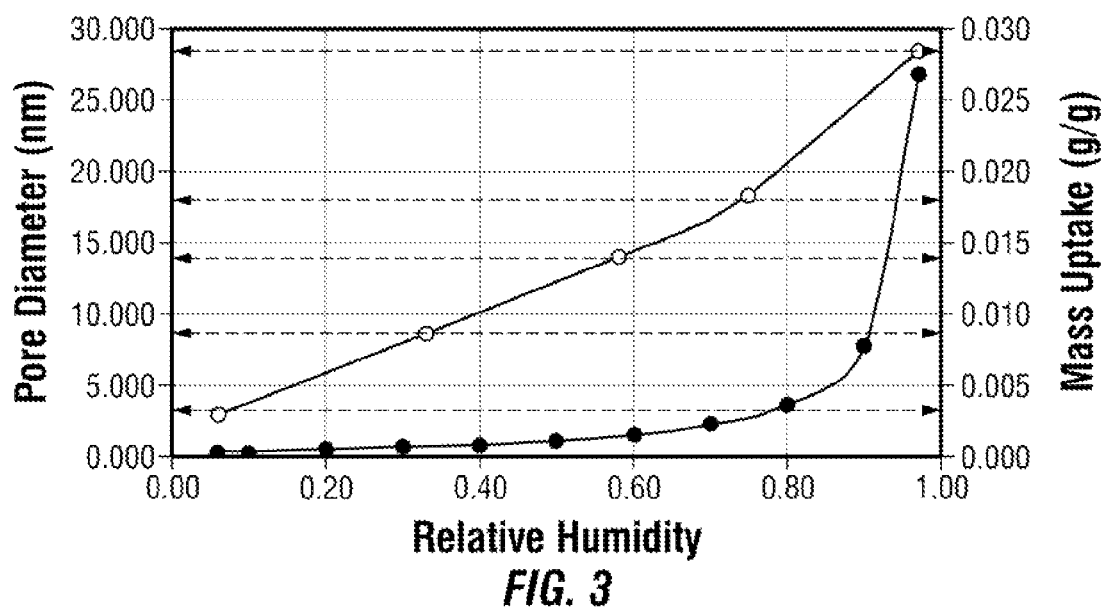
FIG. 3 shows a graphical representation of pore diameters according to one or more embodiments.

Once the grams of fluid uptake or grams of fluid loss are determined, these results can be plotted against relative humidity of the test fluid, and the pore size distribution can be estimated therefrom. The pore size distribution may in particular be determined from mass uptake data by plotting mass uptake and results from the Kelvin equation versus relative humidity as shown in FIG. 3 and as described further below. Once the pore size distribution is estimated, calculations of permeability, including both absolute and relative permeabilities, can occur, as discussed further below. These calculations may allow for a simulation or model to be run so as to determine a saturation profile of material which may then enable an operator to predict or estimate fluid flow behavior for the sample, which can be used to predict or estimate fluid flow behavior for a formation, such as a subterranean formation. The predicted or estimated fluid flow behavior may then be used to design a treatment for the formation. It should be noted that the estimations, calculations, predictions, simulations, and modeling techniques described herein, in some embodiments, may be performed by any suitable processor(s), microprocessor(s), computing system(s), or the like.

To illustrate the breadth of the subject matter explained above, the following discussion further identifies the subject matter with reference to a particular sample. The subject matter particularly relates to a hydration test according to some embodiments.

A sample of Mancos Shale outcrop was ground and dried until it reaches a constant weight at 60° C. After grinding and drying the sample, the sample was split into five substantially equal portions. The portions were weighed. After weighing, each of the samples was exposed to an environment where the humidity was controlled using saturated solutions of five different salts. A vessel containing, the saturated salt solution and the sample is then closed to establish an equilibrium vapor pressure. The pores involved in the resultant condensation will be determined by the relative humidity.

Mass measurements of the samples were taken at various intervals. Then, the amount of grams of water taken up by the sample, per gram of sample, was recorded.

FIG. 1 shows the mass of water adsorbed per mass of the sample versus time. In each of the samples, the masses became stable after about 53 days. The relative humidity in these cases was kept below about 98%. At this relative humidity, the condensation of water onto the surface of the particles can be avoided. The samples were found to appear visually dry and free flowing.

Figure 2:
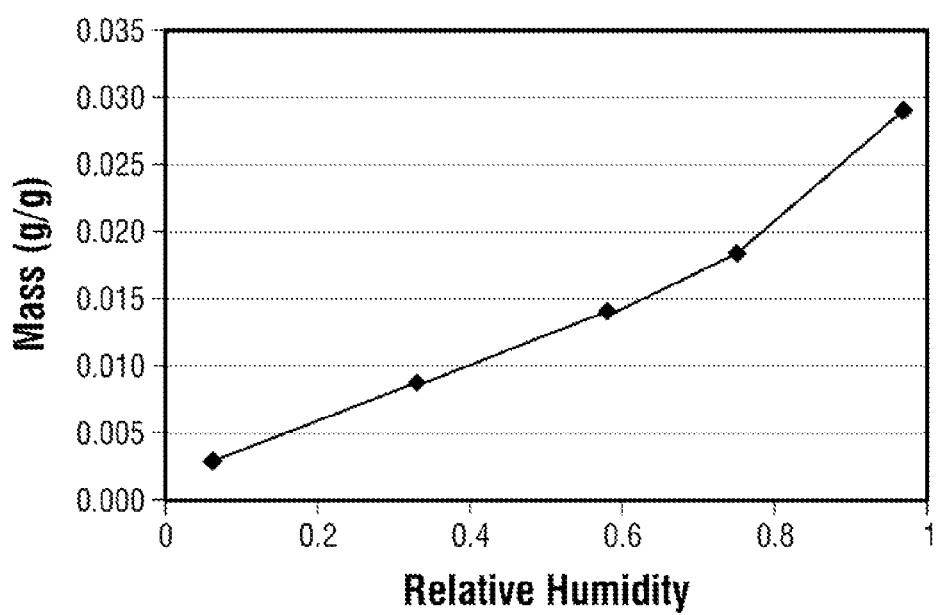
FIG. 2 shows a graphical representation of mass gained versus relative humidity according to one or more embodiments.

FIG. 2 shows a graph of the total mass gained, per gram of sample, versus the relative humidity. The distribution of pore sizes can be estimated based upon the data as explained below.

The pore size distribution can be estimated when a contact angle is known or assumed. Using the Kelvin equation, the capillaries of various sizes, $r_e$, can be shown to fill differentially as the relative humidity of the environment is changed.

$$r_c = \frac{-2\gamma\cos\theta V_{mol}}{RT\ln(P/P_0)}$$

where $\gamma$ (N/m) is the surface tension, $\theta$ (degrees) is the contact angle, $V_{mol}$ is the molar volume of the liquid (m³/mole), R (J/mole K) is the gas constant, and $P_0$ is the equilibrium pressure that would result if a container were evacuated and then partially filled with a liquid at temperature T(K).

For example, when water is used as a test fluid, and the water perfectly wets the porous medium (e.g., using, a contact angle of 0°), the following example provides for a capillary size estimation.

$$r_c = \frac{-2(0.072\text{N/m})(18 \times 10^{-6} \text{ m}^3/\text{mole})}{[8.314(\text{J/moleK})298\text{K}]\ln(0.9)} = 0.996 \times 10^{-3} \text{ m} = 9.96 \text{ nm}$$

It may be understood that condensation of water would occur in capillaries whose diameters are less than about 20 nm. In calculating the capillary size, it should be noted that the contact angle is often assumed to be zero. However, other approximations for contact angle, may be used when water is the test fluid and the medium is hydrophobic.

FIG. 3 shows a plot of pore diameter and mass uptake vs. relative humidity. The data is data from FIG. 2 combined with the output from the Kelvin equation, and can be used to approximate a pore size distribution of the sample. In this approximation, a value of 67° was used as the contact angle. A contact angle can be selected based upon when the diameter of the smallest pore is similar, but slightly larger than the collision diameter of a molecule of the test fluid. The contact angle 67° was determined based upon adjusting a contact angle until the diameter of the smallest pore was about 0.29 nm. This diameter is slightly larger than the collision diameter of the water molecule which is 0.275 nm. Accordingly, the contact angle of 67° was found to be representative of the matrix pores, and the ensuing calculations can be considered applicable estimates for both wettability and pore size distributions. Such a contact angle may vary from other imbibition tests known in the art, such as the test described in "*Moving Beyond the Capillary Suction Time Test,*" SPE 151832 to Pagels et al., which is hereby incorporated by reference. However, the contact angle arrived at by the present example establishes similar wettability determinations as other tests, such as the test described in Pagels.

The test data and calculated properties are reproduced in Table 1.

TABLE 1

| Relative Humidity (decimal) | Saturation (%) | Δ Mass (g) | Capillary Diameter (nm) | Porosity (decimal) |
|---|---|---|---|---|
| 0.06 | 0.10 | 0.002981 | 0.29 | 0.0075 |
| 0.33 | 0.30 | 0.005634 | 0.74 | 0.0141 |
| 0.58 | 0.49 | 0.005406 | 1.50 | 0.0136 |
| 0.75 | 0.64 | 0.004301 | 2.84 | 0.0108 |
| 0.97 | 1.00 | 0.010143 | 26.84 | 0.0254 |

Table 1 also shows contributions to total pore volume from the pores of various sizes. Knowing the pore volume associated with pores of a given size may allow for determination of porosity contributed by those pores, referred to here as $\phi_i$. The sum of the porosity values in this Example is 0.07. Thus, the method described herein provides an estimate of the total accessible porosity.

Further, determining the pore size and porosity associated with that pore size may allow for calculation of a contribution of the pores to a permeability. The expression for permeability, reproduced below, is derived from the bundle of capillaries model.

$$k_i = \frac{r_i^2 \varphi_i}{8}$$

The absolute permeability may be determined as the sum of the $k_i$. The absolute permeability for the Mancos Shale used, in this example, calculated by $\Sigma_i^N k_i$ where N is the total number of data points and is determined by the number of samples tested at a different relative humidity, was calculated to be 582 nanodarcies.

Table 1 additionally shows the saturations attained, at equilibrium, at various relative humidities. The saturation can be considered the fraction of total accessible pore volume that is occupied by condensed water. Using the saturation data, capillary size or pore size data, along with the contact angle allows for the straightforward calculation of capillary pressure so that a capillary pressure vs. saturation plot can be made. Such a plot is often required input for a reservoir simulator.

Specifically, with knowledge of the capillary size $r_e$ and the contact angle, the capillary pressure $p_e$ may be computed by the Laplace equation, reproduced below.

$$p_c = \frac{2\gamma \cos\theta}{r_c}$$

Figure 4:
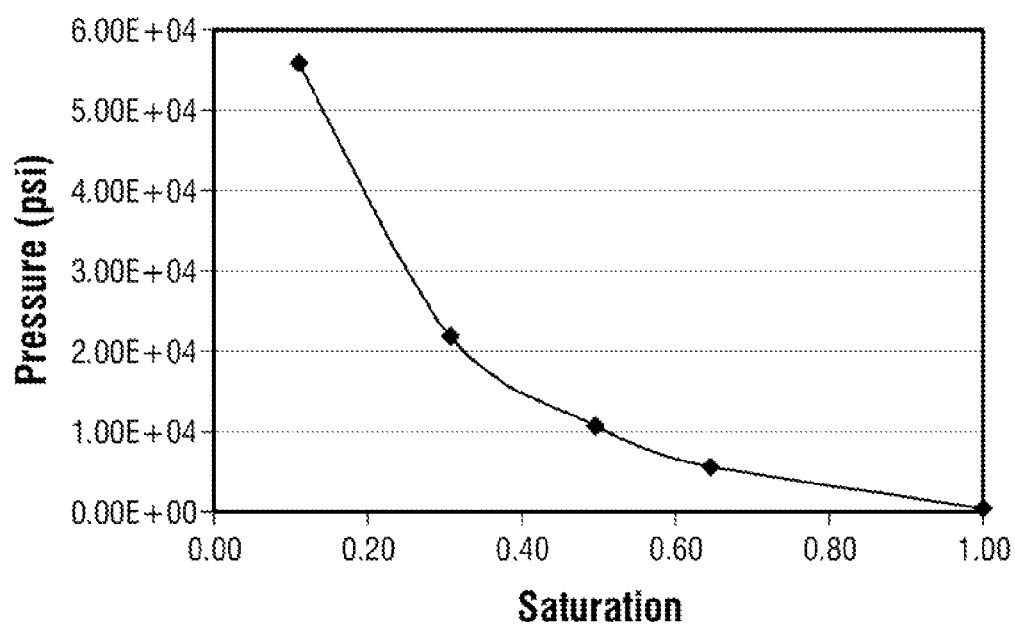
FIG. 4 shows a graphical representation of capillary pressure versus saturation according to one or more embodiments.

FIG. 4 shows capillary pressure versus saturation using the estimated contact angle of 67°. The threshold pressure shown is the lowest pressure at which wetting fluid may be displaced by non-wetting fluid from a porous material that is completely saturated with the wetting fluid. The threshold pressure for the sample of this example was calculated to be 608 psi. Further, using this method, the capillary pressure associated with the smallest pores was estimated to be approximately 56,200 psi. This large pressure would likely lead to structural changes and large uncertainty for pore structure parameters if the sample was probed with mercury. Though the present example did not involve any probing of the sample with mercury, the calculated absolute permeability, porosity and threshold pressure are in agreement with values calculated by other known methods.

Further, relative permeability, which is the ratio of effective permeability of a given phase at a given saturation to the absolute permeability, may be estimated using the following technique and based upon the characteristics and other properties determined from the hydration or desiccation tests performed as described above. When a given group of capillaries is saturated with water, it may be assumed that this group of capillaries allows just water to flow, and that the other capillaries will accommodate just gas flow. Thus, points on the relative permeability curve can be calculated. Further, on the basis of the fact that permeability should vary smoothly from one point to the next, the lines connecting the points may be considered to approximate the behavior at intermediate saturations where both phases are flowing.

Figure 5:
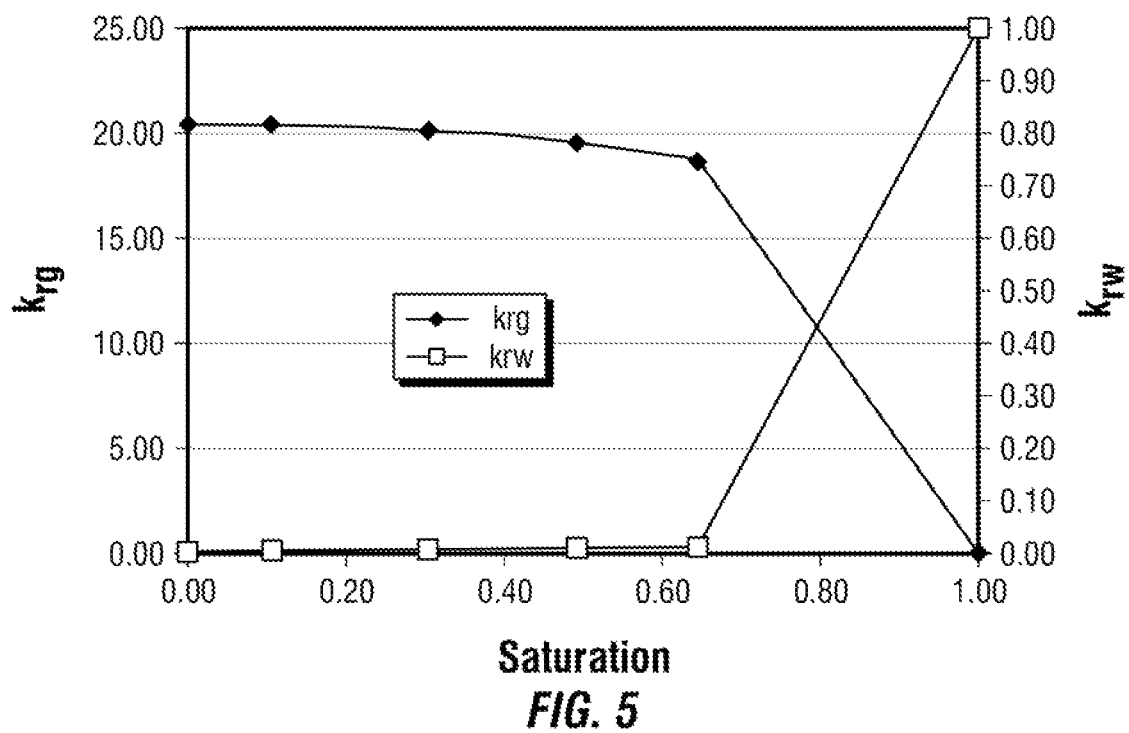
FIG. 5 shows a graphical representation of relative permeability according to one or more embodiments.

FIG. 5 presents an estimate of the relative permeability behavior associated with capillaries of the sample of this example. The non-inertial, non-Darcy flow processes in this example cause the gas permeability at low saturation to be approximately 20 times greater than would be measured using a liquid at a saturation of 1. Because measurements of steady-state flow of liquids through certain samples, such as ultra-low permeability samples, are tedious, a gas such as helium may be used. If unconventional flow behavior is not accounted for, the estimate of absolute permeability would be erroneous, but the calculations provided by the present example would allow for accurate estimation.

The relative permeability behavior of a shale sample at assumed reservoir conditions of 200° F. and 2000 psi was estimated. A relative permeability to gas of greater than 1 is expected, even at reservoir conditions, due to the very small pore sizes associated with an ultra-low permeability shale sample and the concomitant positive contribution to flow due to non-inertial, non-Darcy processes.

Since reservoir conditions change throughout the life of the reservoir, the model presented herein may further allow for inclusion of pressure and temperature dependent effects. Such pressure- and temperature-dependent effects may be modeled using microflow model that is based upon the Knudsen number, which is a ratio of the mean free path length of the gas molecule to the diameter of the pore. These effects may further accurately be used to predict relative permeabilities of any gaseous species.

Once the model has been generated, the model may be used to assist in downhole operations. For example, the determined porosities may allow for a determination of an amount of hydrocarbons that may be stored. Further, determining permeabilities may allow for a determination of the rate at which a fluid will flow downhole in a subterranean formation at a given pressure.

Although the preceding description has been described herein with reference to particular means, materials and embodiments, it is not intended to be limited to the particulars disclosed herein; rather, it extends to all functionally equivalent structures, methods and uses, such are within the scope of the appended claims.

What is claimed is:

1. A method comprising:
    performing, with a test fluid, a desiccation or hydration test on at least a sample of the mesoporous material;
    analyzing characteristics of the mesoporous material to determine the properties of the sample of a mesoporous material; and
    determining, via a processor, fluid flow for a formation based on the properties of the mesoporous material.

2. The method according to claim 1, wherein the analyzing of the characteristics is used to estimate pore size distribution of the mesoporous material.

3. The method according to claim 2, wherein the sample is weighed at predetermined time intervals until a mass increase of the sample is no longer observed, such intervals being used to determine grams of fluid uptake per grant of sample.

4. The method according to claim 3, further comprising comparing the grams of fluid uptake per gram of sample with a size of at least one capillary where condensation occurs.

5. The method according to claim 4, wherein a contact angle is varied until a size of a smallest pore is close to a collision diameter of a molecule of the test fluid.

6. The method according to claim 5, further comprising determining a permeability associated with the at least one capillary based upon the pore size distribution.

7. The method according to claim 6, further comprising determining a relative permeability associated with the at least one capillary based upon the pore size distribution.

8. The method according to claim 7, further comprising determining a rate at which a fluid will flow downhole at a given pressure based on the determined permeability.

9. The method according to claim 4, further comprising determining the pore size distribution based upon the comparison of the grams of fluid uptake per gram of sample with the size of the at least one capillary where condensation occurs.

10. The method according to claim 1, wherein the sample of the mesoporous material is a whole core, a comminuted core, or cuttings.

11. The method according to claim 10, wherein the sample of the mesoporous material is a comminuted core.

12. The method according to claim 1, wherein the performing the desiccation or hydration test further comprises:
 splitting the sample of the mesoporous material; and
 exposing the split sample to an environment where the relative humidity and/or vapor pressure of a test fluid is controlled.

13. The method according to claim 1, wherein the test fluid is water.

14. The method according to claim 13, wherein the performing the desiccation or hydration test comprises:
 splitting the sample of the mesoporous material; and
 exposing the split sample to an environment where the relative humidity and/or vapor pressure of a test fluid is controlled.

15. The method according to claim 14, further comprising exposing the sample to an environment where the relative humidity is controlled, wherein the relative humidity is controlled by saturating the water with a salt to form a saturated mixture, and the saturated mixture is held at a constant temperature and stirred.

16. The method according to claim 1, further comprising:
 inputting at least one of the properties of the sample of the mesoporous material into a model, and
 obtaining, based upon the results of the model, an estimation of a rate at which a fluid will flow downhole at a given pressure.

17. A method for determining pore size distribution of a mesoporous material, comprising:
 performing, with a test fluid, a hydration test on at least a sample of the mesoporous material;
 analyzing characteristics of the sample of the mesoporous material to thereby estimate the pore size distribution; and
 determining, via a processor, fluid flow for a formation based on the pore size distribution of the mesoporous material.

18. A method for determining the pore size distribution of a mesoporous material, comprising:
 performing, with water as a test fluid, a hydration test on at least a sample of the mesoporous material, the performing the hydration test further comprising:
 splitting the sample of the mesoporous material;
 exposing the sample to an environment where the relative humidity of a test fluid is controlled by the water with a salt to form a saturated mixture and controlling a temperature of the saturated mixture;
 analyzing characteristics of the sample of the mesoporous material to thereby estimate the pore size distribution; and
 determining, via a processor, fluid flow for a formation based on properties of the mesoporous material.

\* \* \* \* \*